United States Patent
Chen et al.

(10) Patent No.: US 10,655,150 B2
(45) Date of Patent: May 19, 2020

(54) METHODS OF MAKING CAPSINOIDS BY BIOSYNTHETIC PROCESSES

(71) Applicant: Conagen Inc., Bedford, MA (US)

(72) Inventors: Hui Chen, Bedford, MA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 16/067,161

(22) PCT Filed: Jan. 6, 2017

(86) PCT No.: PCT/US2017/012535
§ 371 (c)(1),
(2) Date: Jun. 29, 2018

(87) PCT Pub. No.: WO2017/120473
PCT Pub. Date: Jul. 13, 2017

(65) Prior Publication Data
US 2019/0010522 A1    Jan. 10, 2019

Related U.S. Application Data

(60) Provisional application No. 62/276,059, filed on Jan. 7, 2016.

(51) Int. Cl.
| | |
|---|---|
| C12P 7/22 | (2006.01) |
| C07C 67/54 | (2006.01) |
| C07C 67/56 | (2006.01) |
| C12N 9/10 | (2006.01) |
| C12N 9/00 | (2006.01) |
| C12N 15/52 | (2006.01) |
| C07C 67/58 | (2006.01) |
| C12P 7/62 | (2006.01) |

(52) U.S. Cl.
CPC ............ *C12P 7/22* (2013.01); *C07C 67/54* (2013.01); *C07C 67/56* (2013.01); *C07C 67/58* (2013.01); *C12N 9/1029* (2013.01); *C12N 9/93* (2013.01); *C12N 15/52* (2013.01); *C12P 7/62* (2013.01)

(58) Field of Classification Search
None
See application file for complete search history.

(56) References Cited

U.S. PATENT DOCUMENTS

| | | | |
|---|---|---|---|
| 6,022,718 | A | 2/2000 | Iwai et al. |
| 7,759,548 | B2 | 7/2010 | Metz et al. |
| 9,371,549 | B2 | 6/2016 | Silverman et al. |
| 9,951,358 | B2 | 4/2018 | Chen et al. |
| 10,392,643 | B2 | 8/2019 | Chen et al. |
| 2003/0145350 | A1 | 7/2003 | Spener et al. |
| 2003/0157670 | A1 | 8/2003 | Nakanishi et al. |
| 2004/0033530 | A1 | 2/2004 | Awrey et al. |
| 2007/0220634 | A1 | 9/2007 | Metz |
| 2007/0244192 | A1 | 10/2007 | Metz |
| 2007/0245431 | A1 | 10/2007 | Metz et al. |
| 2007/0261138 | A1 | 11/2007 | Graham |
| 2008/0213413 | A1 | 9/2008 | Ito et al. |
| 2010/0152291 | A1 | 6/2010 | Amino et al. |
| 2010/0256413 | A1 | 10/2010 | González Molinillo et al. |
| 2011/0166371 | A1 | 7/2011 | Kisaka et al. |
| 2013/0005003 | A1 | 1/2013 | Roessler et al. |
| 2013/0029387 | A1 | 1/2013 | Nikolau et al. |
| 2014/0248668 | A1 | 9/2014 | Raghavan et al. |
| 2014/0371477 | A1 | 12/2014 | Wood et al. |
| 2016/0138061 | A1 | 5/2016 | Haas et al. |
| 2016/0168603 | A1 | 6/2016 | Garg et al. |
| 2016/0273014 | A1 | 9/2016 | Chen et al. |
| 2017/0247733 | A2 | 8/2017 | Chen et al. |

FOREIGN PATENT DOCUMENTS

| | | |
|---|---|---|
| CN | 103087998 A | 5/2013 |
| CN | 10/3173444 A | 6/2013 |
| CN | 103725652 A | 4/2014 |
| IN | 402 009 A1 | 10/2009 |
| JP | 2003-210164 A | 8/2007 |
| JP | 2013-116104 A | 6/2013 |
| WO | WO 98/00557 A2 | 1/1998 |
| WO | WO 03/087321 A2 | 10/2003 |
| WO | WO 2006/100680 A2 | 9/2006 |
| WO | WO 2008/034648 A1 | 3/2008 |
| WO | WO 2009/157376 | 12/2009 |
| WO | WO 2013/006953 A1 | 1/2013 |
| WO | WO 2013/ 021261 A2 | 2/2014 |
| WO | WO 2015/066615 A1 | 5/2015 |
| WO | WO 2015/109168 A1 | 7/2015 |

(Continued)

OTHER PUBLICATIONS

De Wulf et al. Bioconversion of vanillin to vanillyl alcohol in a two phase reactor. 1989, Enzyme Engineering and Biotechnology, vol. 20/21: p. 165-180, The Humana Press, Inc.*
International Search Report and Written Opinion for Application No. PCT/US2017/012535 dated Mar. 23, 2017.
Kobata et al., Potent production of capsaicinoids and capsinoids by Capsicum peppers. J Agric Food Chem. Nov. 20, 2013;61(46):11127-32. doi: 10.1021/jf403553w. Epub Nov. 6, 2013.
[No Author Listed], Invitrogen S.O.C. Medium Catalog No. 15544-034. 2002. 1 page.
Ashrafi et al., De novo assembly of the pepper transcriptome (Capsicum annuum): a benchmark for in silico discovery of SNPs, SSRs and candidate genes. BMC Genomics. Oct. 30, 2012;13(571):1-15.

(Continued)

*Primary Examiner* — Iqbal H Chowdhury
(74) *Attorney, Agent, or Firm* — Wolf, Greenfield & Sacks, P.C.; Karen K. Chan

(57) ABSTRACT

Provided herein are methods of making capsinoids including providing a capsiate synthase in a mixture or cellular system, feeding 8-methyl-6-nonenoyl-CoA, 6E-8-methylnonenoic acid or 8-methylnonanoic acid into the mixture or cellular system, feeding vanillyl alcohol into the mixture or cellular system, and collecting capsinoids from the mixture or cellular system.

21 Claims, 7 Drawing Sheets
Specification includes a Sequence Listing.

(56) References Cited

FOREIGN PATENT DOCUMENTS

| WO | WO 2015/160842 A1 | 10/2015 |
| WO | WO 2018/017772 | 7/2016 |
| WO | WO 2018/119343 | 12/2016 |

OTHER PUBLICATIONS

Aza-Gonzalez et al., Molecular biology of capsaicinoid biosynthesis in chili pepper (*Capsicum* spp.). Plant Cell Rep. May 2011, vol. 30, No. 5, p. 695-706.

Del Rosario Abraham-Juárez M et al., Virus-induced silencing of Comt, pAmt and Kas genes results in a reduction of capsaicinoid accumulation in chili pepper fruits. Planta. Feb. 2008;227(3):681-95. Epub Nov. 13, 2007.

Fujino et al., Molecular identification and characterization of two medium-chain acyl-CoA synthetases, MACS1 and the Sa gene product. J Biol Chem. Sep. 21, 2001;276(38):35961-6. Epub Jul. 24, 2001.

GenBank Accession No. JW054178.1. Sep. 1, 2012. 1 page.

Geneseq database accession No. ADL72268. Shockey et al. Oct. 23, 2003.

Geneseq database accession No. ADL72357. Shockey et al. Oct. 23, 2003.

Kozik et al., CLPY5434.bl_C15.ab1 CLP(XYZ) lettuce perennis Lactuca perennis cDNA 25 clone CLPY5434, mRNA sequence. Genbank entry [online]. National Center for Biotechnolgy. Information. Oct. 6, 2006, [Retrieved on Mar. 23, 2018]. Retrieved from the Internet: <URL:https://www.ncbi.nlm.nih.gov/nucest/DW094259.1 ?report=genbank>; 2 pages.

Lee et al., Molecular cloning of a novel pathogen-inducible cDNA encoding a putative acyl-CoA synthetase from *Capsicum annuum* L. Plant Mol Biol. Aug. 2001;46(6):661-71.

Mazourek et al., A dynamic interface for capsaicinoid systems biology. Plant Physiol. Aug. 2009;150(4):1806-21. doi: 10.1104/pp.109.136549. Epub Jun. 24, 2009.

NCBI Reference Sequence: XP 016564091.1. May 5, 2016. 1 page.

Prasad et al., Influence of 8-methyl-nonenoic acid on capsaicin biosynthesis in in-vivo and in-vitro cell cultures of *Capsicum* spp. J Agric Food Chem. Mar. 8, 2006;54(5):1854-9.

Prasad et al., Characterization of capsaicin synthase and identification of its gene (csy1) for pungency factor capsaicin in pepper (*Capsicum* sp.). Proc Natl Acad Sci U S A. Sep. 5, 2006;103(36):13315-20. Epub Aug. 28, 2006. Erratum in: Proc Natl Acad Sci U S A. Apr. 17, 2007;104(16):6876. Retraction in: Prasad et al., Proc Natl Acad Sci U S A. Dec. 23, 2008;105(51):20558.

Prasad et al., Valine pathway is more crucial than phenyl propanoid pathway in regulating capsaicin biosynthesis in Capsicum frutescens mill. J Agric Food Chem. Sep. 6, 2006;54(18):6660-6.

Qin et al., Whole-genome sequencing of cultivated and wild peppers provides insights into Capsicum domestication and specialization. Proc Natl Acad Sci U S A. Apr. 8, 2014;111(14):5135-40. doi: 10.1073/pnas.1400975111. Epub Mar. 3, 2014.

Ramachandra et al., Biotransformation of isoeugenol to vanilla flavour metabolites and capsaicin in suspended and immobilized cell cultures of Capsicum frutescens: study of the influence of β-cyclodextrin and fungal elicitor. Process Biochem. Nov. 1999;35(3-4):341-348.

Ruan et al., Capsicum annuum cultivar Yidu-Red inbred 201 acyltransferase (Pun1) mRNA, complete cds. GenBank Accession No. GU300812.1. Dated Jan. 17, 2010. [https://www.ncbi.nlm.nih.gov/nuccore/283766072].

Shockey et al., *Arabidopsis* contains a large superfamily of acyl-activating enzymes. Phylogenetic and biochemical analysis reveals a new class of acyl-coenzyme a synthetases. Plant Physiol. Jun. 2003;132(2):1065-76.

Simbaqueb A et al., Development and characterization of microsatellite markers for the Cape gooseberry Physalis peruviana. PLoS One. 2011;6(10):e26719. doi: 10.1371/journal.pone.0026719. Epub Oct. 21, 2011.

Stewart et al., Genetic control of pungency in C. chinense via the Pun1 locus. J Exp Bot. 2007;58(5):979-91. Epub Mar. 5, 2007.

Stewart et al., The Pun1 gene for pungency in pepper encodes a putative acyltransferase. Plant J. Jun. 2005;42(5):675-88.

Sudhakar Johnson et al., Biotransformation of ferulic acid and vanillylamine to capsaicin and vanillin in immobilized cell cultures of Capsicum frutescens. Plant Cell Tiss Organ Cult. Feb. 1996;44(2):117-121.

Thalemine AT4G23850—Gene LACS4. Retrieved from< https://apps.araport.org/thalemine/portal.do?externalids=AT4G23850 >on Apr. 1, 2018.

Thiel et al., "Chili Pepper Fruits: Presumed Precursors of Fatty Acids Characteristic for Capsaicinoids", J. Agric. Food Chem. 2008, 56, 4219-4224.

UniProt Accession No. Q58VTO "UniProtKB—Q58VTO (Q58VTO_CAPCH) Acyltransferase, 34, 35/34, 61Pun1, Capsicum chinense—protein sequence" Apr. 26, 2005 [located online Nov. 16, 2017 athttp://www.uniprot.org/uniproVQ58VTO].

UniProt Accession No. B5LAV6 "Putative Long Chain acyl-CoA synthetase" (Oct. 14, 2008) [retrieved on Nov. 13, 2017 from http://www.uniprot.org/uniprot/B5LAV6] p. 2, sequence.

UniProt Accession No. Q6F4D5 "Glycosyltransferase" (Aug. 16, 2004) [retrieved on 13 62 Nov. 2017 from http://www.uniprot.org/uniprot/Q6F4D5] p. 2, sequence.

WPI database AN 2014-K94081. Apr. 16, 2014. CN 103 725 652 A.

\* cited by examiner

Molecular structures of capsiate, dihydrocapsiate, and nordihydrocapsiate

Capsiate synthase (CS)-catalyzed capsiate biosynthesis in sweet peppers.

HPLC profiles of putative capsiate (CQ) and dihydrocapsiate (DHCQ) production for 6E-8-methylnonenoic acid (6E) and 8-methylnonanoic acid (8M), respectively. The VA (Vanilyl alcohol), 6E and 8M concentrations are 500 mg/L.

CQ and DHCQ production from VA+6E (VE) and VA+8M (VM), respectively. The experiment was performed in triplicates.

GC/MS profiles of CQ, DHCQ cultures and DHCQ standard.

METHODS OF MAKING CAPSINOIDS BY BIOSYNTHETIC PROCESSES

CROSS-REFERENCE TO RELATED APPLICATIONS

This application is a national stage filing under U.S.C. § 371 of PCT International Application No. PCT/US2017/012535, with an international filing date of Jan. 6, 2017, which claims priority to U.S. Provisional Application No. 62/276,059, filed on Jan. 7, 2016, the contents of each of which are incorporated by reference herein in their entirety.

FIELD OF THE INVENTION

The present invention relates to methods of making capsinoids, including capsiate, dihydrocapsiate, nordihydrocapsiate biosynthetically, principally in a cellular system.

BACKGROUND OF THE INVENTION

Capsinoids, which include capsiate, dihydrocapsiate, and nordihydrocapsiate, are molecules naturally present in chili peppers (*Capsicum annuum* L.). Capsiate is mainly found in a non-pungent cultivar of red pepper, CH19 Sweet, and is known to provide effects comparable to capsaicin, including activation of the capsaicin receptor. Capsinoids were first isolated in a unique variety of chili peppers, CH-19 Sweet, which does not contain capsaicin (Yazawa et al., 1989).

Capsinoids are capsaicinoid-like substances, which, as noted above, were first reported in the fruits of a non-pungent cultivar of pepper (*Capsicum annuum* L.), named CH-19 Sweet (Yazawa et al., 1989). Later, capsiate (4-hydroxy-3-methoxybenzyl (E)-8-methyl-6-nonenoate), dihydrocapsiate (4-hydroxy-3-methoxybenzyl 8-methylnonanoate), and nordihydrocapsiate (4-hydroxy-3-methoxybenzyl 7-methyloctanoate) were identified as the three major capsinoids in CH-19 Sweet (Kobata et al., 1998; Kobata et al., 1999). In capsinoids, the aromatic portion of capsaicinoids, vanillylamine, is replaced by vanillyl alcohol whereas their acyl residues are identical to those of corresponding capsaicinoids.

Previously capsaicinoids have been reported to promote energy metabolism, suppress body-fat accumulation and have the potential to provide a dietetic therapy for obesity and diabetes. However, capsaicin is strongly pungent and neurotoxic, which largely prohibits its administration to humans (Masuda et al., 2003). In contrast, capsiate can be taken in large amounts without pain and its effect on energy metabolism and weight loss mimic that of capsaicin (Masuda et al., 2003; Snitker et al., 2009). Today capsiate and CH-19 Sweet Pepper Extract are widely used as a dietary supplement to boost metabolism.

While capsinoids are structurally similar to capsaicin, the substance that causes pungency in hot peppers, capsinoids are significantly less pungent. Capsinoids are known to have an estimated "hot taste threshold" that is about $1/1000$ that of capsaicin. Structural differences between capsaicin and members of the capsinoid family are shown in FIG. 1. Capsinoids have an ester bond in their structures as compared with the amide bond of capsaicin.

Capsaicin is believed to activate sensory receptors on the tongue that are used to detect thermal heat (Szallasi, et al. 1999). These receptors, Transient Receptor Potential Vanilloid 1 (TRPV1), are also present in the stomach and other organs (Nagy, et al. 2004). Activation of TRPV1 receptors is understood to trigger the sympathetic nervous system (SNS) (Iwai, et al., 2003). Capsaicin may mediate an increase in fat burning in humans and animals through activating the SNS.

Like capsaicin, capsinoids activate sensory receptors such as Transient Receptor Potential Vanilloid 1 (TRPV1) receptors (Iida et al., 2003). Capsaicin and capsinoids may mediate an increase in fat burning in humans and animals through activating the SNS. However, unlike capsaicin, capsinoids do not initiate the heat sensation in the mouth, which may be because capsinoids cannot physically reach the TRPV1 receptors in the oral cavity due to structural differences compared to capsaicin. Nonetheless, capsinoids can activate TRPV1 receptors in the stomach, which has been shown to be important for the metabolic effects of both capsaicin and capsinoids (Ohnuki et al., 2001).

These metabolic effects are believed to contribute to the many health beneficial properties of both capsaicin and capsinoids, including anticancer, anti-inflammatory, and analgesic activities, as well as weight management (Macho et al., 2003; Sancho et al., 2002; He et al., 2009; Kawabata, et al. 2006; Handler, et al 2008). Studies have shown that both energy metabolism (Snitker et al., 2009; Inoue et al., 2007) and body temperature (Ohnuki et al., 2001; Hachiya, et al., 2007) elevations occur in humans following the administration of capsinoids or extracts of CH-19 Sweet. Moreover, body fat accumulation is suppressed following capsinoids intake (Ohnuki et al., 2001).

However, the contents of capsinoids in sweet peppers are extremely low. For example, only one pound of capsinoids can be extracted from 10,000 pounds of CH-19 Sweet peppers, which are expensive, drive the market price for capsiate, resulting in the price of capsiate extracted from sweet peppers to be extremely expensive e.g., US $600-25,000 for capsiate at 40% to 98% purity; alibaba.com/product-detail/High-quality-Capsiate-40-to-98_344832645.html?spm=a2700.7724838.35.1.J77Yht. Accordingly, more effective methods of producing capsinoids in a significant amount are desired.

BRIEF SUMMARY OF THE INVENTION

The disclosure is directed to methods of making capsinoids, e.g., using mixtures or cellular systems as described herein.

In some aspects, a method of producing a capsinoid is provided, the method comprising expressing a capsiate synthase (CS) in a cellular system; adding 8-methyl-6-nonenoyl-CoA and vanillyl alcohol to the cellular system; and incubating the cellular system for a sufficient time to produce the capsinoid. In other aspects, a method of producing dihydrocapsiate is provided, the method comprising expressing a capsiate synthase (CS) and an acyltransferase (ACS) in a cellular system; adding 8-methylnonanoic acid and vanillyl alcohol to the cellular system; and incubating the cellular system for a sufficient time to produce the dihydrocapsiate. In yet other aspects, a method of producing capsiate is provided, the method comprising expressing a capsiate synthase (CS) and an acyltransferase (ACS) in a cellular system; adding 6E-8-methylnonenoic acid and vanillyl alcohol to the cellular system; and incubating the cellular system for a sufficient time to produce the capsiate. In another aspect, a method of producing a capsinoid is provided, the method comprising expressing a capsiate synthase (CS) and an acyltransferase (ACS) in a cellular system; adding a medium chain fatty acid and vanillyl alcohol to the cellular system; and incubating the cellular system for a sufficient time to produce the capsinoid.

In some embodiments of any one of the above methods, the CS amino acid sequence is derived from a plant of the *Capsicum* genus. In some embodiments, the *Capsicum* genus plant is a ghost chili plant. In some embodiments, the CS comprises an amino acid sequence having at least 90% identity to SEQ ID NO: 1. In some embodiments, the CS comprises the amino acid sequence of SEQ ID NO: 1.

In some embodiments of any one of the above methods, the ACS amino acid sequence is derived from a plant of the *Capsicum* genus. In some embodiments, the *Capsicum* genus plant is a ghost chili plant. In some embodiments, the ACS comprises an amino acid sequence having at least 90% identity to SEQ ID NO: 2. In some embodiments, the ACS comprises the amino acid sequence of SEQ ID NO: 2.

In some embodiments of any one of the above methods, the cellular system is selected from the group including yeast, non-capsinoid producing plants, algae and bacteria. In some embodiments, the cellular system is bacteria. In some embodiments, the cellular system is *E. Coli*.

In some embodiments of any one of the above methods, the method further comprises collecting the produced capsinoid, capsiate or dihydrocapsiate. In some embodiments, the method further comprises purifying the produced capsinoid, capsiate or dihydrocapsiate to a purity of greater than 70%. In some embodiments, the purifying step comprises acid-base extraction. In some embodiments, the purifying step comprises vacuum distillation. In some embodiments, the purifying step comprises semi-preparative HPLC.

In yet other aspects, a method of producing a capsinoid is provided, the method comprising providing a capsiate synthase (CS) in a reaction mixture; adding 8-methyl-6-nonenoyl-CoA and vanillyl alcohol to the reaction mixture; and incubating the reaction mixture for a sufficient time to produce the capsinoid. In some aspects, a method of producing dihydrocapsiate is provided, the method comprising providing a capsiate synthase (CS) and an acyltransferase (ACS) in a reaction mixture; adding 8-methylnonanoic acid and vanillyl alcohol to the reaction mixture; and incubating the reaction mixture for a sufficient time to produce the dihydrocapsiate. In another aspect, a method of producing capsiate is provided, the method comprising providing a capsiate synthase (CS) and an acyltransferase (ACS) in a reaction mixture; adding 6E-8-methylnonenoic acid and vanillyl alcohol to the reaction mixture, and incubating the reaction mixture for a sufficient time to produce the capsiate. In yet another aspect, a method of producing a capsinoid is provided, the method comprising providing a capsiate synthase (CS) and an acyltransferase (ACS) in a reaction mixture; adding a medium chain fatty acid and vanillyl alcohol to the reaction mixture; and incubating the reaction mixture for a sufficient time to produce the thereby producing the capsinoid.

In some embodiments of any one of the above methods, the CS amino acid sequence is derived from a plant of the *Capsicum* genus. In some embodiments, the *Capsicum* genus plant is a ghost chili plant. In some embodiments, the CS comprises an amino acid sequence having at least 90% identity to SEQ ID NO: 1. In some embodiments, the CS comprises the amino acid sequence of SEQ ID NO: 1.

In some embodiments of any one of the above methods, the ACS amino acid sequence is derived from a plant of the *Capsicum* genus. In some embodiments, the *Capsicum* genus plant is a ghost chili plant. In some embodiments, the ACS comprises an amino acid sequence having at least 90% identity to SEQ ID NO: 2. In some embodiments, the ACS comprises the amino acid sequence of SEQ ID NO: 2.

In some embodiments of any one of the above methods, the CS and/or ACS are produced in a cellular system selected from the group including yeast, non-capsinoid producing plants, algae and bacteria. In some embodiments, the cellular system is bacteria. In some embodiments, the cellular system is *E. Coli*.

In some embodiments of any one of the above methods, the method further comprises collecting the produced capsinoid, capsiate or dihydrocapsiate from the reaction mixture. In some embodiments, the method further comprises purifying the produced capsinoid, capsiate or dihydrocapsiate to a purity of greater than 70%. In some embodiments, the purifying step comprises acid-base extraction. In some embodiments, the purifying step comprises vacuum distillation. In some embodiments, the purifying step comprises semi-preparative HPLC.

The disclosure also provides the following additional embodiments. In some embodiments, a bioconversion method of making capsinoid is provided comprising providing a capsiate synthase (CS) in a mixture; feeding 8-methylnonanoyl-CoA in the mixture; feeding vanillyl alcohol to the mixture; and collecting capsinoid. In some embodiments, a bioconversion method of making capsiate is provided comprising providing a capsiate synthase (CS) in a mixture; providing an acyltransferase in the mixture; feeding 6E-8-methylnonenoic acid; feeding vanillyl alcohol to the mixture; and collecting capsiate. In some embodiments, a bioconversion method of making dihydrocapsiate is provided comprising providing a capsiate synthase (CS) in a mixture; providing an acyltransferase in the mixture; feeding 8-methylnonanoic acid; feeding vanillyl alcohol to the mixture; and collecting capsiate. In some embodiments, a bioconversion method of making capsinoid is provided comprising expressing a CS gene in a cellular system; expressing an ACS1 gene in the cellular system; feeding a medium chain fatty acid to the cellular system; feeding vanillyl alcohol to the cellular system; collecting capsinoid.

BRIEF DESCRIPTION OF THE DRAWINGS

As shown in FIG. 3, different products were formed from 6E and 8M, respectively.

DETAILED DESCRIPTION

Definitions

Figure 1:
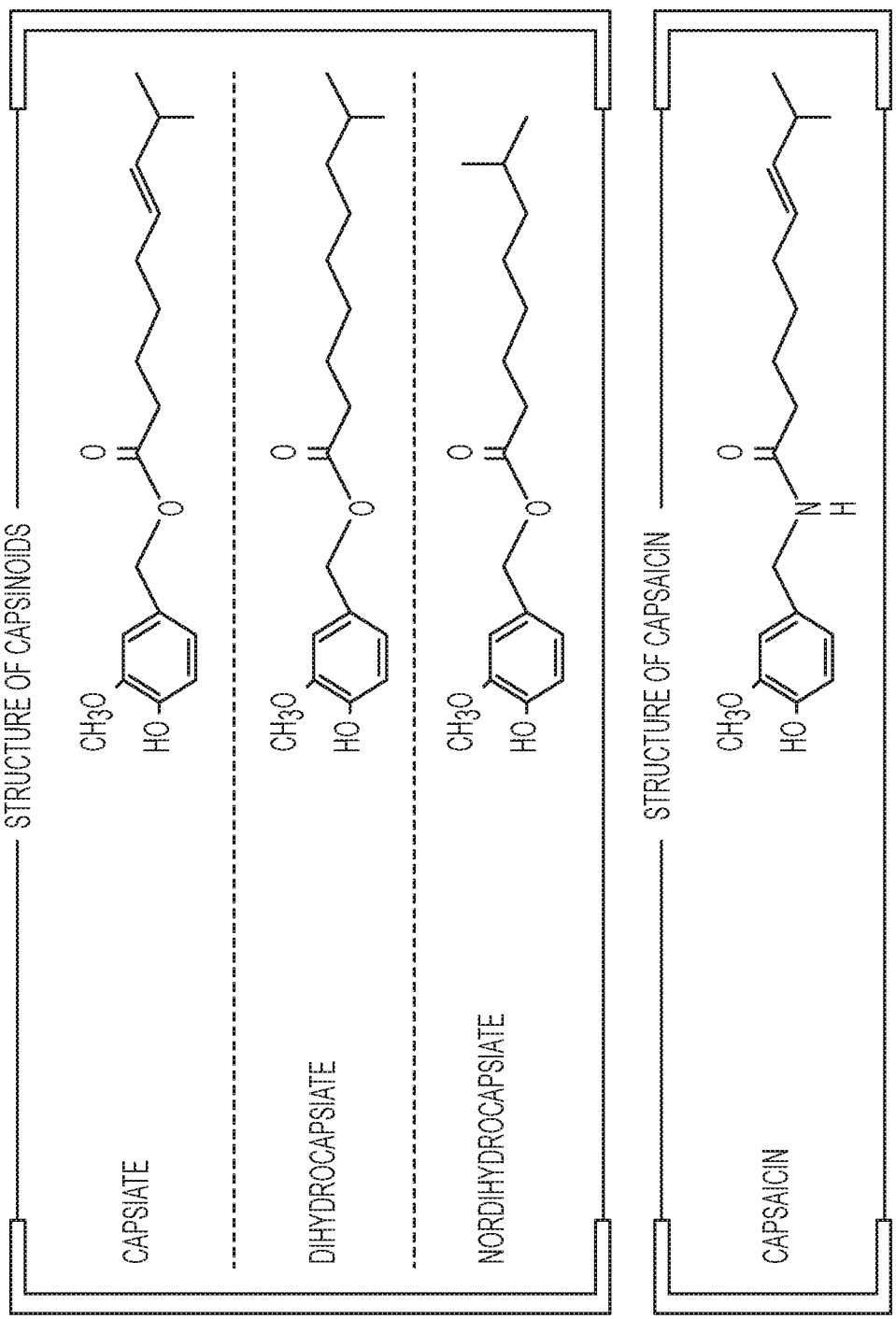
FIG. 1 shows the molecular structures for capsiate, dihydrocapsiate, and nordihydrocapsiate.

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

"Percent (%) amino acid sequence identity" with respect to the variant polypeptide sequences of the subject technology refers to the percentage of amino acid residues in a candidate sequence that are identical with the amino acid residues of a reference polypeptide after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

Unless specified otherwise, the percent identity of two polypeptide or polynucleotide sequences refers to the percentage of identical amino acid residues or nucleotides across the entire length of the shorter of the two sequences.

"Transformation" is used according to its ordinary and customary meaning as understood by a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are used according to their ordinary and customary meanings as understood by a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule.

The terms "recombinant," "heterologous," and "exogenous," when used herein in connection with polynucleotides, are used according to their ordinary and customary meanings as understood by a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The term "cellular system" as used herein refers to any cells that provide for the expression of ectopic proteins. It includes bacteria, yeast, plant cells and animal cells. It includes prokaryotic and eukaryotic cells. It also includes in vitro expression of proteins utilizing cellular components, such as ribosomes.

The term "growing the cellular system" as used herein includes providing medium that would allow cells to multiply and divide. It also includes providing resources so that cells or cellular components can translate and make recombinant proteins.

The term "protein expression" as used herein refers to protein production as part of gene expression. It consists of the stages after DNA has been transcribed to messenger RNA (mRNA). The mRNA is then translated into polypeptide chains, which are ultimately folded into proteins. DNA is present in the cells through transfection, a process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells.

Transduction is often used to describe virus-mediated DNA transfer. Transformation, transduction, and viral infection are included under the definition of transfection for this application. In addition, protein expression includes in vitro translation, wherein proteins are expressed utilizing cellular organelles that are outside the cells.

The term "bioconversion," also known as "biotransformation," as used herein refers to the use of live organisms often microorganisms (e.g., bacteria and yeast) to carry out a chemical reaction that may be more costly or not feasible nonbiologically. These organisms convert a substance to a chemically modified form.

The term "reaction mixture" and "mixture," as used herein, refers to the physical combination of two or more substances which may be mixed in the form of solutions, suspensions, or colloids with many variations known in the art. A reaction mixture may comprise a mixture of recombinant proteins (e.g., an ACS and a CS as described herein) and one or more in vitro reaction system components such as substrates (e.g., vanillyl alcohol (VA), 6E-8-methylnonenoic acid (6E), and/or 8-methylnonanoic acid (8M) as described herein), buffers (e.g., potassium phosphate buffer), and salts (e.g., $MgCl_2$). For example, Applicants used an HPLC-based method to measure the activity of pepper ACSI (Chen et al., 2011). In such system the reaction mixture (400 µE) contained 0.1 M Tris-HCl, pH 7.5, 2 mM DTT, 5 mM ATP, 10 mM $MgCl_2$, 0.5 mM CoA, 0.1% Triton and 200 µM carboxylic acids. The reaction was initiated by adding 20 µm of purified enzyme and stopped after 30 minutes by addition of 20 micromolar acetic acid. HPLC was performed with Dionex-UltiMate© 3000 LC Systems (Thermo Scientific) using an Acclaim® 120 CI 8 reversed-phase column (Thermo Scientific; 3µ, 120 A, 150×3 mm). The mobile phase consisted of solvent A (0.1% trifluoroacetic acid) and solvent B (acetonitrile). The gradient elution procedure was as follows: 0 to 5 min, 5% of B; 5 to 9 min, a linear gradient from 5 to 80% of B; 9 to 11 min, 80% of B; 11 to 12 min, 5% of B. The flow rate was 0.6 ml/min. The diode array detector collected data in the 200- to 400-nm range. For detection and quantification of substrate and products, peak areas were measured at 257 nm.

The use of the words "a" or "an" when used in conjunction with the term "comprising" herein may mean "one," but it is also consistent with the meaning of "one or more," "at least one," and "one or more than one."

Figure 2:
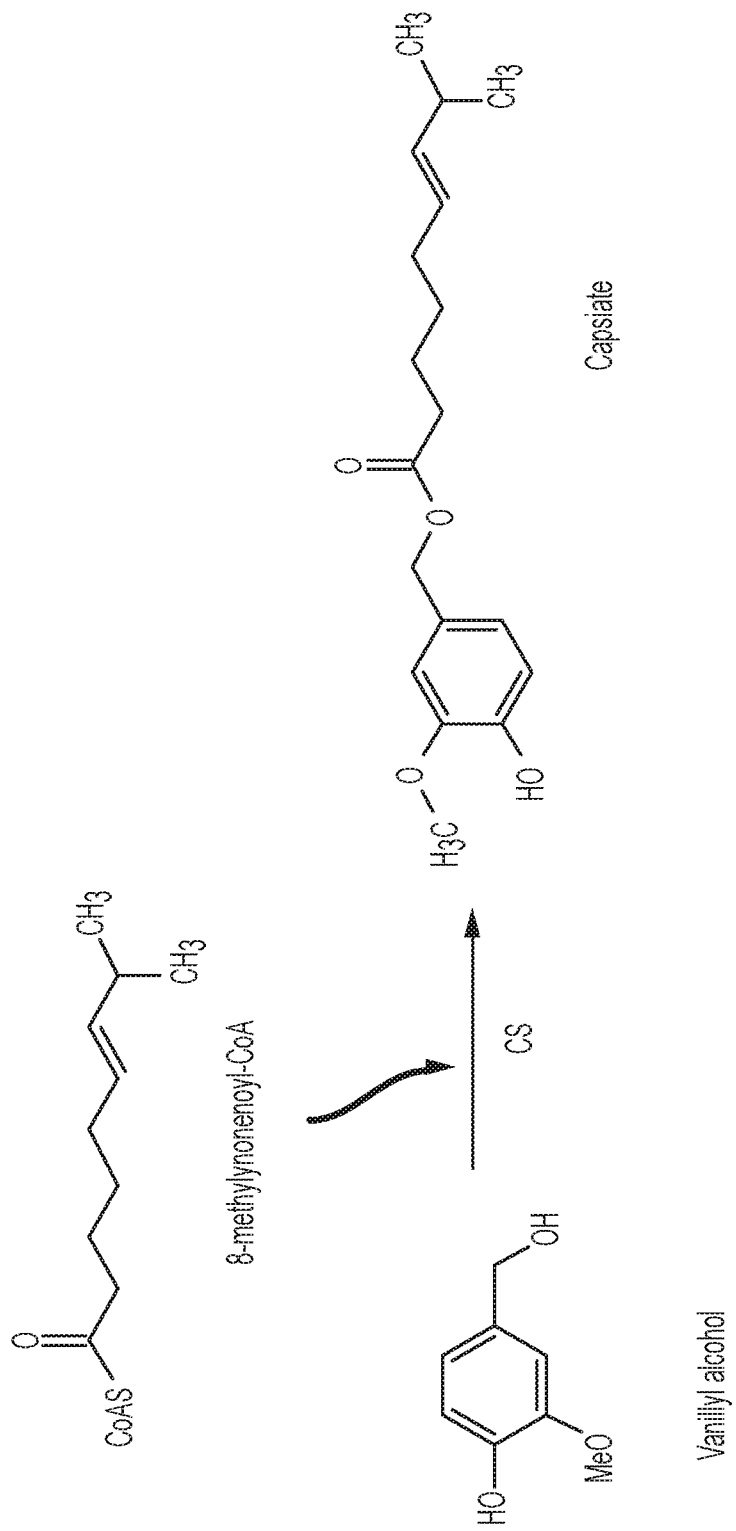
FIG. 2 shows a diagram Capsiate synthase (CS)-catalyzed capsiate biosynthesis.

As described above, capsinoids, like capsiate and capsinoids present in CH-19 Sweet Pepper Extract, are widely used for many purposes but are currently incredibly expensive to produce. Capsiate is believed to be naturally synthesized in peppers by capsiate synthase (CS, also referred to as capsaicin synthase), an acyltransferase that transfers the 8-methyl-6-nonenoyl moiety from 8-methyl-6-nonenoyl-CoA to vanillyl alcohol to form an ester conjugate (FIG. 2) and genetically, its biosynthesis is controlled by the Pun1 locus in pepper (Han et al., 2013).

As described herein, it has been found that expression systems that utilize an acyl-CoA synthetase (ACS), such as ghost pepper ACS1, and a capsiate/capsaicin synthase (CS), such as ghost pepper AT3/PUN1, can be used to produce capsinoids when fed appropriate starting materials, such as vanillyl alcohol (VA) and either 6E-8-methylnonenoic acid (6E) or 8-methylnonanoic acid (8M).

Cellular Systems

Figure 3:
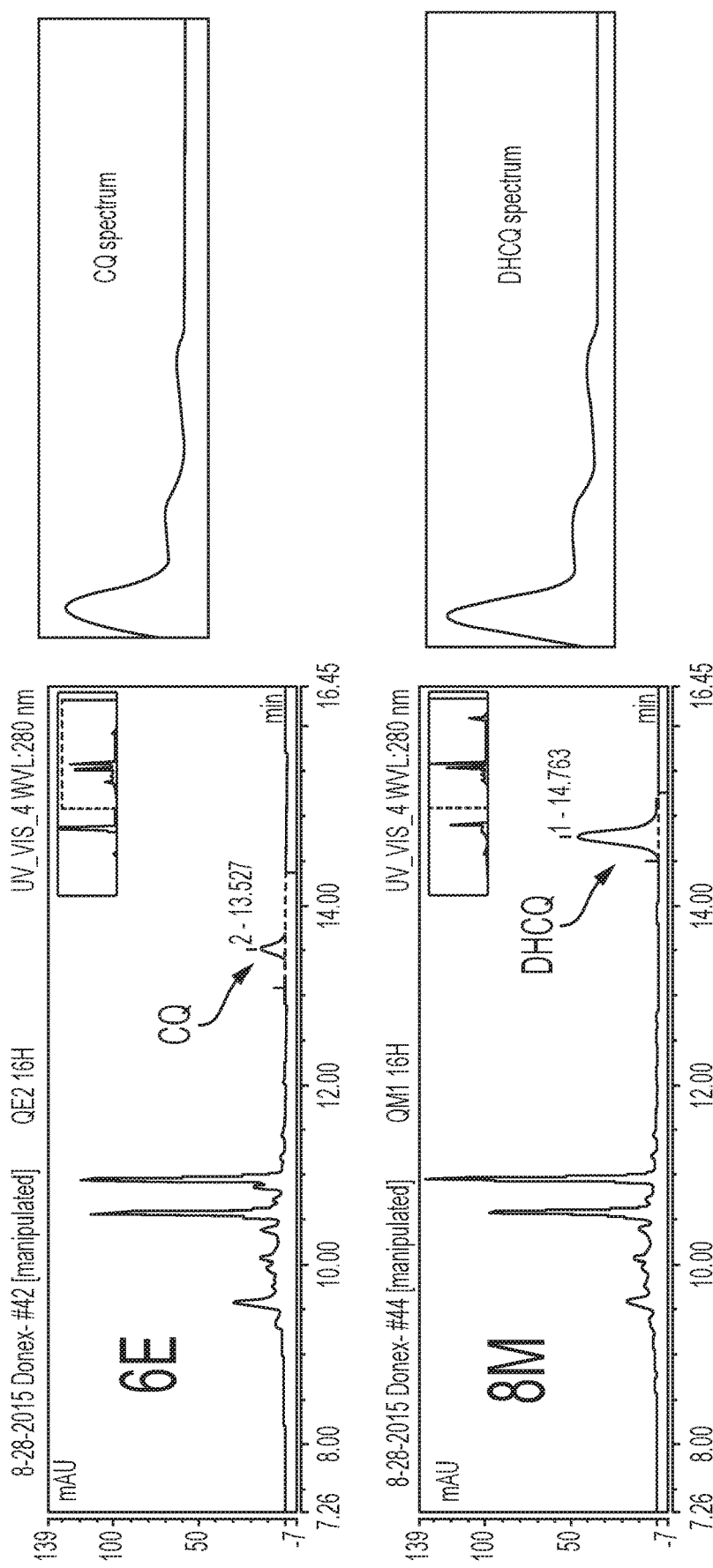
FIG. 3 shows the HPLC profiles of putative capsiate (CQ) and dihydrocapsiate (DHCQ) production from 6E-8-methylnonenoic acid (6E) and 8-methylnonanoic acid (8M), respectively. The VA (vanillyl alcohol), 6E and 8M concentrations are 500 mg/L.

In some aspects, the present disclosure is directed to the production of capsinoids in cellular systems, such as in bacterial or fungal cells. In some embodiments, the cellular system is *E. coli* cultures overexpressing ghost pepper ACS1 and AT3/PUN1 genes. Use of ghost pepper ACS1 and AT3/PUN1 has been described previously for the production of capsaicinoids (see, e.g., PCT/US2015/011729, published as PCT Application Publication No. WO2015109168, which is herein incorporated by reference in its entirety). Capsaicinoids, as described above, are structurally and functionally distinguishable from capsinoids. As shown in FIG. 3, different capsinoid products were formed from the introduction of 6E-8-methylnonenoic acid (6E) with vanillyl alcohol (VA) or 8M with VA. More quantitative data showed that this ACS1-PUN1 system prefers 8M as a substrate (FIG. 3).

In some embodiments, a method of producing a capsinoid is provided, the method comprising expressing a capsiate synthase (CS) in a cellular system; adding 8-methyl-6-nonenoyl-CoA and vanillyl alcohol (together or separately) to the cellular system; and incubating the cellular system for a sufficient time to produce the capsinoid. In some embodiments, a method of producing dihydrocapsiate is provided, the method comprising expressing a capsiate synthase (CS) and an acyltransferase (ACS) in a cellular system; adding 8-methylnonanoic acid and vanillyl alcohol (together or separately) to the cellular system; and incubating the cellular system for a sufficient time to produce the dihydrocapsiate. In some embodiments, a method of producing capsiate is provided, the method comprising expressing a capsiate synthase (CS) and an acyltransferase (ACS) in a cellular system; adding 6E-8-methylnonenoic acid and vanillyl alcohol (together or separately) to the cellular system; and incubating the cellular system for a sufficient time to produce the capsiate. In some embodiments, a method of producing a capsinoid is provided, the method comprising expressing a capsiate synthase (CS) and an acyltransferase (ACS) in a cellular system; adding a medium chain fatty acid and vanillyl alcohol (together or separately) to the cellular system; and incubating the cellular system for a sufficient time to produce the capsinoid.

Exemplary cellular systems include yeast cells (*Pichia Pastoris* or *Saccharomyces cerevisiae*), plants or plant cells (e.g., non-capsinoid producing plants or plant cells such as *Arabidopsis thaliana*, *Oryza Sativa* or *Zea mays*), algal cells, and bacterial cells (e.g., *Escherichia coli*).

The amount of time sufficient to produce a capsinoid of interest will vary depending on the capsinoid being produced, the type of cellular system used, and the conditions under which the cellular system is maintained. Exemplary conditions for producing capsinoids in bacteria are provided in the Examples. Similar conditions may be adapted for yeast, such as *Saccharomyces cerevisiae*, which have been shown to be capable of producing many molecules biosynthetically (see, e.g., PCT Application Publication No. WO2014086842). Conditions described herein may also be adapted for use with plant cells, which have also been shown to be capable of producing many molecules biosynthetically (see, e.g., PCT Application Publication No. WO2010124324).

Another embodiment of the present disclosure is a bioconversion method of making capsinoid comprising expressing a CS gene in a cellular system, expressing an ACS1 gene in the cellular system, feeding a medium chain fatty acid to the cellular system, feeding vanillyl alcohol to the cellular system, and collecting capsinoid.

In some embodiments of any of the cellular systems provided herein, a capsiate synthase (CS) may be used. In some embodiments, the CS nucleic acid and/or amino acid sequence are derived from a plant of the *Capsicum* genus (e.g., a ghost chili plant or CH19 Sweet plant). In some embodiments, the CS comprises an amino acid sequence having at least 75%, at least 80%, at least 85%, at least 90%, at least 95%, at least 96%, at least 97%, at least 98%, at least 99%, or 100% identity to SEQ ID NO: 1. In some embodiments, the CS consists of the amino acid sequence of SEQ ID NO: 1. In some embodiments, the CS is encoded by a nucleic acid sequence having at least 75%, at least 80%, at least 85%, at least 90%, at least 95%, at least 96%, at least 97%, at least 98%, at least 99%, or 100% identity to SEQ ID NO: 3.

```
Exemplary amino acid sequence of ghost chili
Pun1/AT3
                                         (SEQ ID NO: 1)
MAFALPSSLVSVCDKSFIKPSSLTPSKLRFHKLSFIDQSLSNMYIPCAFF

YPKVQQRLEDSKNSDELSHIANLLQTSLSQTLVSYYPYAGKLKDNATVDC

NDMGAEFLSVRIKCSMSEILDHPHASLAESIVLPKDLPWANNCEGGNLLV

VQVSKFDCGGIAISVCFSHKIGDGCSLLNFLNDWSSVTRDHTTTALVPSP

RFVGDSVFSTKKYGSLITPQILSDLNECVQKRLIFPTDKLDALRAKVAEE

SGVKNPTRAEVVSALLFKCATKASSSMLPSKLVHFLNIRTMIKPRLPRNA

IGNLSSIFSIEATNMQDMELPTLVRNLRKEVEVAYKKDQVEQNELILEVV

ESMREGKLPFENMDGYENVYTCSNLCKYPYYTVDFGWGRPERVCLGNGPS

KNAFFLKDYKAGQGVEARVMLHKQQMSEFERNEELLEFIA
```

In some embodiments of any of the cellular systems provided herein, an acyltransferase (ACS) may be used. In some embodiments, the ACS nucleic acid and/or amino acid sequence are derived from a plant of the *Capsicum* genus (e.g., a ghost chili plant or CH19 Sweet plant). In some embodiments, the ACS comprises an amino acid sequence having at least 75%, at least 80%, at least 85%, at least 90%, at least 95%, at least 96%, at least 97%, at least 98%, at least 99%, or 100% identity to SEQ ID NO: 2. In some embodiments, the ACS consists of the amino acid sequence of SEQ ID NO: 2. In some embodiments, the ACS is encoded by a nucleic acid sequence having at least 75%, at least 80%, at least 85%, at least 90%, at least 95%, at least 96%, at least 97%, at least 98%, at least 99%, or 100% identity to SEQ ID NO: 4.

```
Exemplary amino acid sequence of ghost chili ACS
                                         (SEQ ID NO: 2)
MATDKFIIEVESAKPAKDGRPSMGPVYRSIFAKHGFPPPIPGLDSCWDIF

RMSVEKYPNNRMLGRREIVDGKPGKYVWMSYKEVYDIVIKVGNSIRSIGV

DVGDKCGIYGANCPEWIISMEACNAHGLYCVPLYDTLGAGAVEFIISHAE

VTIAFVEEKKLPELLKTFPNASKYLKTIVSFGKVTPEQKKELEEFGVVLY

SWDEFLQLGSGKQFDLPVKKKEDICTIMYTSGTTGDPKGVLISNTSIVTL

IAGVRRFLGSVDESLNVDDVYLSYLPLAHIFDRVIEECFIHHGASIGFWR

GDVKLLTEDIGELKPTVFCAVPRVLDRIYSGLQQKIAAGGFLKSTLFNLA

YAYKHHNLKKGRKHFEASPLSDKVVFSKVKEGLGGRVRLILSGAAPLAAH

VEAFLRVVACCHVLQGYGLTETCAGTFVSLPNRYDMLGTVGPPVPNVDVC

LESVPEMSYDALSSTPRGEVCVRGDVLFSGYYKREDLTKEVMIDGWFHTG

DVGEWQPNGSLKIIDRKKNIFKLSQGEYVAVENLENIYGNNPIIDSIWIY

GNSFESFLVAVINPNQRAVEQWAEVNGLSGDFASLCEKPEVKEYILRELT

KTGKEKKLKGFEFLKAVHLDPVPFDMERDLLTPTFKKKRPQLLKYYKDVI

DSMYKGTK
```

Reaction Mixtures

The present disclosure is also directed, in part, to the production of capsinoids using reaction mixtures (e.g., in vitro reaction mixtures) comprising the an ACS, such as ghost pepper ACS1, and/or a CS, such as ghost pepper AT3/PUN1, to which appropriate starting materials (e.g., VA and 6E or VA and 8M) are added.

In some embodiments, a method of producing a capsinoid is provided, the method comprising providing a capsiate synthase (CS) in a reaction mixture; adding 8-methyl-6-nonenoyl-CoA and vanillyl alcohol (together or separately) to the reaction mixture; and incubating the reaction mixture for a sufficient time to produce the capsinoid. In some embodiments, a method of producing dihydrocapsiate is provided, the method comprising providing a capsiate synthase (CS) and an acyltransferase (ACS) in a reaction mixture; adding 8-methylnonanoic acid and vanillyl alcohol (together or separately) to the reaction mixture; and incubating the reaction mixture for a sufficient time to produce the dihydrocapsiate. In some embodiments, a method of producing capsiate is provided, the method comprising providing a capsiate synthase (CS) and an acyltransferase (ACS) in a reaction mixture; adding 6E-8-methylnonenoic acid and vanillyl alcohol (together or separately) to the reaction mixture, and incubating the reaction mixture for a sufficient time to produce the capsiate. In some embodiments, a method of producing a capsinoid, the method comprising providing a capsiate synthase (CS) and an acyltransferase (ACS) in a reaction mixture; adding a medium chain fatty acid and vanillyl alcohol (together or separately) to the reaction mixture; and incubating the reaction mixture for a sufficient time to produce the thereby producing the capsinoid. It is to be understood that components of the reaction mixture may be added in any order, together or separately, as long as the resulting reaction mixture is capable of producing the desired capsinoid once incubated.

The enzymes for use in the reaction mixture can be produced from any source, preferably recombinantly, e.g., in *E. coli* or another suitable host cell capable of producing the enzymes, or synthetically. The reaction mixture may be a buffered solution containing the enzymes and other components, such as starting materials (e.g., VA and 6E or VA and 8M) and salts, which may be appropriate for producing a desired capsinoid. The reaction mixture may also contain or be made up of a cell lysate (e.g., an *E. coli* or yeast cell lysate) to which additional components such as starting materials (e.g., VA and 6E or VA and 8M) may be added.

In some embodiments of any of the reaction mixtures provided herein, a capsiate synthase (CS) may be used. In some embodiments, the CS nucleic acid and/or amino acid sequence are derived from a plant of the *Capsicum* genus (e.g., a ghost chili plant or CH19 Sweet plant). In some embodiments, the CS comprises an amino acid sequence having at least 75%, at least 80%, at least 85%, at least 90%, at least 95%, at least 96%, at least 97%, at least 98%, at least 99%, or 100% identity to SEQ ID NO: 1. In some embodiments, the CS consists of the amino acid sequence of SEQ ID NO: 1.

In some embodiments of any of the reaction mixtures provided herein, an acyltransferase (ACS) may be used. In some embodiments, the ACS nucleic acid and/or amino acid sequence are derived from a plant of the *Capsicum* genus (e.g., a ghost chili plant or CH19 Sweet plant). In some embodiments, the ACS comprises an amino acid sequence having at least 75%, at least 80%, at least 85%, at least 90%, at least 95%, at least 96%, at least 97%, at least 98%, at least 99%, or 100% identity to SEQ ID NO: 2. In some embodiments, the ACS consists of the amino acid sequence of SEQ ID NO: 2.

The amount of time sufficient to produce a capsinoid of interest will vary depending on the capsinoid being produced, the type of reaction mixture used, and the conditions under which the reaction mixture is incubated. Exemplary conditions for the biosynthetic production molecules using reaction mixtures are known in the art (see, e.g., PCT Application Publication No. WO2016/054534, which is herein incorporated by reference in its entirety).

An embodiment of the present disclosure is a bioconversion method of making capsinoid comprising providing a capsiate synthase (CS) in a mixture, feeding 8-methyl-6-nonenoyl-CoA in the mixture, feeding vanillyl alcohol to the mixture; and collecting capsinoid.

Another embodiment of the present disclosure is a bioconversion method of making capsiate comprising providing a capsiate synthase (CS) in a mixture, providing an acyltransferase in the mixture, feeding 6E-8-methylnonenoic acid, feeding vanillyl alcohol to the mixture, and collecting capsiate.

Another embodiment of the present disclosure is a bioconversion method of making dihydrocapsiate comprising providing a capsiate synthase (CS) in a mixture, providing an acyltransferase in the mixture, feeding 8-methylnonanoic acid, feeding vanillyl alcohol to the mixture, and collecting capsiate.

Purification

In some embodiments of any of the methods provided herein, the method may further comprise purifying a capsinoid (e.g., a capsiate or dihydrocapsiate). In some embodiments, the capsinoid is purified to a purity of between 50% and 100% by weight. In some embodiments, the capsinoid is purified to a purity of greater than 60%, greater than 70%, greater than 80%, greater than 90%, greater than 95%, greater than 96%, greater than 97%, greater than 98% or greater than 99% pure by weight. A capsinoid of interest may be purified by any method known in the art or described herein. Exemplary methods include acid-base extraction, vacuum distillation and semi-preparative HPLC (see, e.g., Li H. X. et al., Food Science Technology, 57: 446 (2014); and, Andrade-Eiroa A., et al., An alternative to trial and error methodology in solid phase extraction: an original automated solid phase extraction procedure for analysing PAHs and PAH-derivatives in soot, RSC Advances 4: pp. 33636-44 (2014).

Compositions

Any of the capsinoids produced by a method described herein may be included in a composition. In some embodiments, composition is an orally consumable product (such as a beverage, food product, dietary supplement, nutraceutical, pharmaceutical composition, dental hygienic composition or cosmetic product) which is contacted with the mouth of man or animal, including substances that are taken into and subsequently ejected from the mouth and substances which are drunk, eaten, swallowed, or otherwise ingested; and that are safe for human or animal consumption when used in a generally acceptable range of concentrations.

As used herein, "dietary supplement(s)" refers to compounds intended to supplement the diet and provide nutrients, such as vitamins, minerals, fiber, fatty acids, amino acids, etc. that may be missing or may not be consumed in sufficient quantities in a diet. Any suitable dietary supplement known in the art may be used. Examples of suitable dietary supplements can be, for example, nutrients, vitamins, minerals, fiber, fatty acids, herbs, botanicals, amino acids, and metabolites.

As used herein, "nutraceutical(s)" refers to compounds, which includes any food or part of a food that may provide medicinal or health benefits, including the prevention and/or treatment of disease or disorder (e.g., fatigue, insomnia, effects of aging, memory loss, mood disorders, cardiovascular disease and high levels of cholesterol in the blood, diabetes, osteoporosis, inflammation, autoimmune disorders, etc.). Any suitable nutraceutical known in the art may be used. In some embodiments, nutraceuticals can be used as supplements to food and beverages and as pharmaceutical formulations for enteral or parenteral applications which may be solid formulations, such as capsules or tablets, or liquid formulations, such as solutions or suspensions.

In some embodiments, dietary supplements and nutraceuticals can further contain protective hydrocolloids (such as gums, proteins, modified starches), binders, film-forming agents, encapsulating agents/materials, wall/shell materials, matrix compounds, coatings, emulsifiers, surface active agents, solubilizing agents (oils, fats, waxes, lecithins, etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

Any suitable pharmaceutical composition known in the art may be used. In certain embodiments, a pharmaceutical composition of the present disclosure can contain a capsinoid and one or more pharmaceutically acceptable excipients. Such compositions can be prepared according to procedures well known in the art, for example, as described in Remington's Pharmaceutical Sciences, Mack Publishing Co., Easton, Pa., USA.

EXAMPLES

Production of Capsinoids in *E. Coli*

ACS1 and AT3/Pun1 genes from ghost chili pepper were co-overexpressed in *E. coli* BL21(DE3) cells as previously described (see, e.g., PCT Application Publication No. WO2015/066615, the contents of which are herein incorporated by reference in their entirety). Plasmid pCDFDuet-ACS1 was used to transform competent *E. coli* BL21 (DE3) cells. The transformed cells were selected on LB plates containing 100 mg/L of spectinomycin. The resulting BL21 (DE3) cells harboring pCDFDuet-ACSI were used for a second transformation with pETite N-His SUMO-ghost Pun1 vector. The transformants were selected on LB plates containing 50 mg/L of kanamycin and 100 mg/L of spectinomycin. The ACS1 and AT3/Pun1 coding sequences used to co-overexpress ACS1 and Pun1 in the transformants are shown below:

Sequence of Pun1/AT3 coding sequence (from ghost chili pepper)
(SEQ ID NO: 3)
ATGGCTTTTGCATTACCATCATCACTTGTTTCAGTTTGTGACAAATCTTT

TATCAAACCTTCCTCTCTCACCCCCTCTAAACTTAGATTTCACAAGCTAT

CTTTCATCGATCAATCTTTAAGTAATATGTATATCCCTTGTGCATTTTTT

TACCCTAAAGTACAACAAAGACTAGAAGACTCCAAAAATTCTGATGAGCT

TTCCCATATAGCCCACTTGCTACAAACATCTCTATCACAAACTCTAGTCT

CTTACTATCCTTATGCAGGAAAGTTGAAGGACAATGCTACTGTTGACTGT

AACGATATGGGAGCTGAGTTCTTGAGTGTTCGAATAAAATGTTCCATGTC

TGAAATTCTTGATCATCCTCATGCATCTCTTGCAGAGAGCATAGTTTTGC

CCAAGGATTTGCCTTGGGCGAATAATTGTGAAGGTGGTAATTTGCTTGTA

GTTCAAGTAAGTAAGTTTGATTGTGGGGAATAGCCATCAGTGTATGCTT

TTCGCACAAGATTGGTGATGGTTGCTCTCTGCTTAATTTCCTTAATGATT

GGTCTAGCGTTACTCGTGATCATACGACAACAGCTTTAGTTCCATCTCCT

AGATTTGTAGGAGATTCTGTCTTCTCTACAAAAAAATATGGTTCTCTTAT

TACGCCACAAATTTTGTCCGATCTCAACGAGTGCGTACAGAAAAGACTCA

TTTTTCCTACAGATAAGTTAGATGCACTTCGAGCTAAGGTGGCAGAAGAA

TCAGGAGTAAAAAATCCAACAAGGGCAGAAGTTGTTAGCGCTCTTCTTTT

CAAATGTGCAACAAAGGCATCATCATCAATGCTACCATCAAAGTTGGTTC

ACTTCTTAAACATACGTACTATGATCAAACCTCGTCTACCACGAAATGCC

ATTGGAAATCTCTCGTCTATTTTCTCCATAGAAGCAACTAACATGCAGGA

CATGGAGTTGCCAACGTTGGTTCGTAATTTAAGGAAGGAAGTTGAGGTGG

CATACAAGAAAGACCAAGTCGAACAAAATGAACTGATCCTAGAAGTAGTA

GAATCAATGAGAGAAGGGAAACTGCCATTTGAAAATATGGATGGCTATGA

GAATGTGTATACTTGCAGCAATCTTTGCAAATATCCGTACTACACTGTAG

ATTTTGGATGGGAAGACCTGAAAGAGTGTGTCTAGGAAATGGTCCCTCC

AAGAATGCCTTCTTCTTGAAAGATTACAAAGCTGGGCAAGGCGTGGAGGC

GCGGGTGATGTTGCACAAGCAACAAATGTCTGAATTTGAACGCAATGAGG

AACTCCTTGAGTTCATTGCCTAA

Sequence of ACS1 coding sequence (from ghost chili pepper)
(SEQ ID NO: 4)
ATGGCTACGACAAATTTATTATTGAAGTTGAATCAGCAAAACCGGCAAA

AGATGGTCGCCCGAGCATGGGCCCGGTCTATCGTTCGATCTTTGCGAAAC

ATGGCTTTCCGCCGCCGATCCCGGGTCTGGATTCATGCTGGGACATTTTT

CGTATGTCGGTGGAAAAATATCCGAACAATCGCATGCTGGGCCGTCGCGA

AATTGTTGATGGCAAACCGGGTAAATACGTTTGGATGAGCTACAAAGAAG

TCTACGACATCGTTATCAAAGTCGGTAACAGTATTCGTTCCATCGGCGTG

GATGTTGGTGACAAATGCGGCATTTATGGTGCAAACTGTCCGGAATGGAT

TATCAGCATGGAAGCATGCAATGCTCATGGCCTGTATTGTGTCCCGCTGT

ACGATACCCTGGGCGCAGGTGCTGTGGAATTTATTATCTCTCACGCGGAA

GTGACCATCGCCTTCGTTGAAGAGAAAAAACTGCCGGAACTGCTGAAAAC

CTTTCCGAATGCGAGCAAATATCTGAAAACCATTGTCTCTTTCGGCAAAG

TGACGCCGGAACAGAAGAAAGAACTGGAAGAATTTGGTGTGGTTCTGTAC

AGTTGGGATGAATTTCTGCAGCTGGGCTCCGGTAAACAATTCGATCTGCC

GGTGAAAAAGAAAGAAGATATTTGCACCATCATGTATACGAGCGGCACCA

CGGGTGATCCGAAAGGTGTGCTGATTTCAAACACCTCGATTGTGACGCTG

ATCGCCGGTGTTCGTCGCTTTCTGGGCTCAGTTGATGAATCGCTGAATGT

GGATGACGTTTATCTGTCATACCTGCCGCTGGCACATATTTTTGACCGTG

TGATCGAAGAATGCTTCATTCATCACGGCGCTTCGATCGGTTTTTGGCGC

GGCGATGTGAAACTGCTGACCGAAGACATTGGCGAACTGAAACCGACGGT

TTTCTGTGCGGTCCCGCGTGTGCTGGATCGCATCTATTCAGGTCTGCAGC

AAAAAATTGCGGCCGGCGGTTTTCTGAAATCGACCCTGTTCAACCTGGCG

TATGCCTACAAACATCACAATCTGAAGAAAGGCCGCAAACACTTTGAAGC

CAGCCCGCTGTCTGATAAAGTCGTGTTCAGTAAAGTGAAAGAAGGCCTGG

GCGGTCGTGTTCGCCTGATTCTGTCCGGTGCGGCTCCGCTGGCCGCACAT

GTGGAAGCGTTTCTGCGTGTTGTCGCCTGCTGTCACGTTCTGCAGGGCTA

TGGTCTGACCGAAACGTGCGCAGGCACCTTCGTGAGTCTGCCGAACCGCT

ACGATATGCTGGGCACGGTTGGTCCGCCGGTCCCGAATGTCGATGTGTGC

CTGGAAAGCGTGCCGGAAATGTCTTATGACGCTCTGAGCTCTACCCCGCG

TGGTGAAGTTTGTGTCCGCGGCGATGTTCTGTTTTCCGGTTATTACAAAC

GTGAAGACCTGACCAAAGAAGTTATGATTGATGGCTGGTTCCATACGGGC

GACGTCGGTGAATGGCAGCCGAACGGTAGCCTGAAAATCATCGATCGTAA

GAAAAACATCTTCAAACTGTCTCAAGGCGAATATGTGGCCGTTGAAAACC

TGGAAAATATTTACGGCAACAATCCGATTATCGACAGCATTTGGATCTAT

GGTAACAGTTTTGAATCCTTCCTGGTCGCGGTGATCAACCCGAATCAGCG

TGCAGTCGAACAATGGGCTGAAGTGAATGGCCTGAGTGGTGATTTCGCCT

CCCTGTGTGAAAAACCGGAAGTGAAAGAATACATTCTGCGCGAACTGACC

AAAACGGGCAAAGAGAAAAAACTGAAAGGTTTCGAATTTCTGAAAGCAGT

TCATCTGGACCCGGTGCCGTTTGATATGGAACGTGACCTGCTGACCCCGA

CGTTCAAGAAAAACGTCCGCAACTGCTGAAATACTATAAAGATGTGATC

GACTCAATGTATAAAGGCACGAAATAA

Next, production of ACS1 and PUN1 was induced in the transformants. Briefly, an overnight culture of the transformants was grown in TB medium (2%) containing 50 mg/L of kanamycin and 100 mg/L of spectinomycin. The overnight culture was then diluted and grown at 37° C. to an OD600 of 0.6 and cooled down to 16° C. Then 1 mM IPTG was added to induce the expression of ACS1 and Pun1. After 1 hour of incubation at 16° C., the following substrates were added to the cultures: either (a) 500 mg/L of vanillyl alcohol (VA) and 500 mg/L of 6E-8-methylnonenoic acid (6E) or (b) 500 mg/L of VA and 500 mg/L of 8-methyl nonanoic acid (8M). The chemical structure of vanillyl alcohol is provided in FIG. 2. The chemical structures of 6E and 8M are provided below.

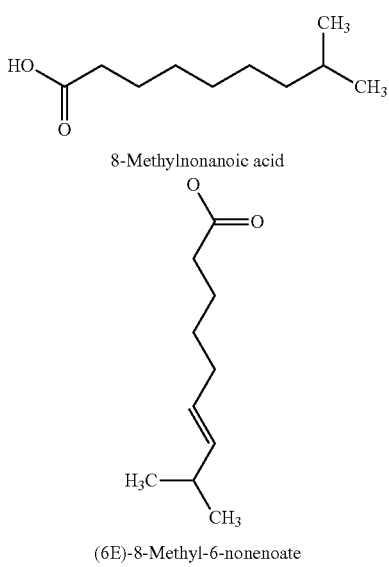

8-Methylnonanoic acid (6E)-8-Methyl-6-nonenoate

Figure 4:
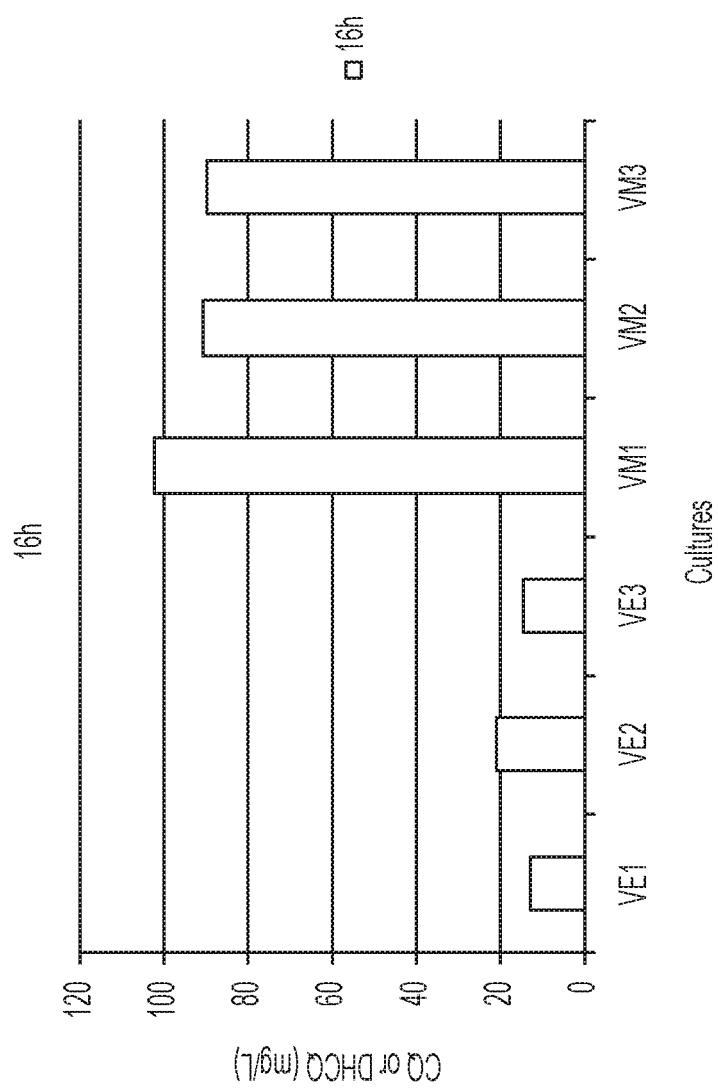
FIG. 4 shows CQ and DHCQ production from VA+6E (VE) and VA+8M (VM), respectively. The experiment was performed in triplicates.

Samples were taken at 16 hours after the feeding of substrates, putative capsiate (CQ) and dihydrocapsiate (DHCQ) were extracted by ethyl acetate, and putative CQ and DHCQ production was measured from the 6E or 8M cultures, respectively (FIG. 3). More quantitative data showed that this ACS1-Pun1 system preferred 8M as a substrate. Production of CQ and DHCQ after 16 hours of induction with 6E+VA or 8M+VA, respectively, was confirmed in triplicate experiments (FIG. 4).

Figure 5:
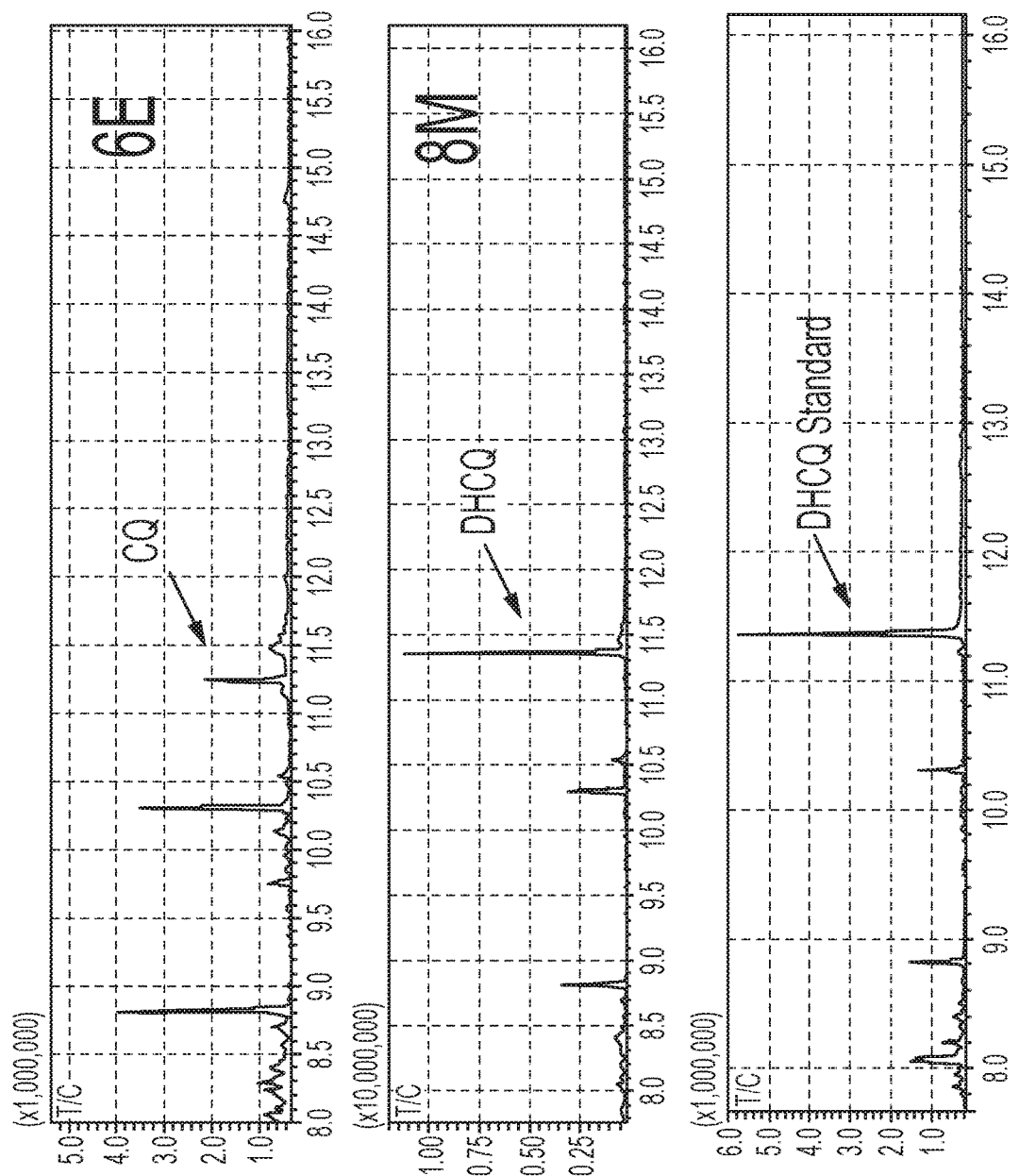
FIG. 5 shows the GC/MS analysis was performed to confirm the identity of CQ and DHCQ in the cultures.
Figure 6:
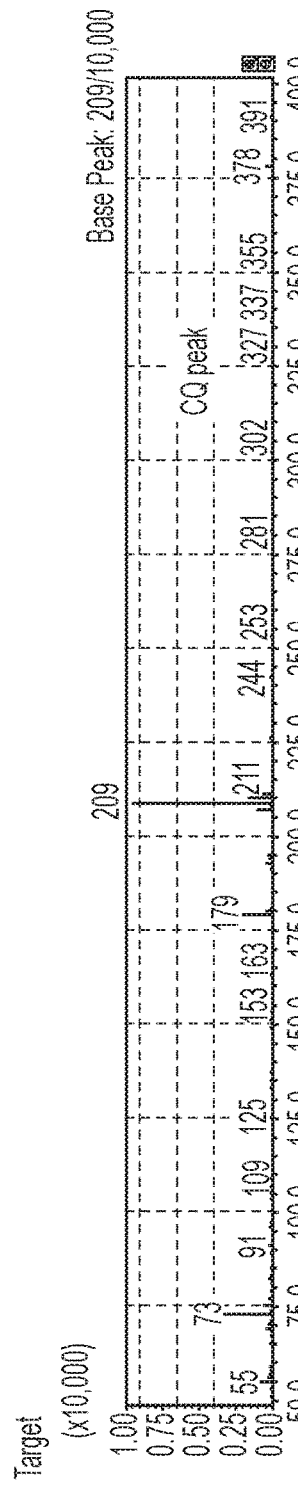
FIG. 6 shows comparisons of DHCP (dihydrocapsaicin) spectra in the GC/MS library with CQ and DHCQ spectra obtained from the induction samples, since there is no CQ and DHCQ spectra in the GC/MS library and the closest match is that of DHCP (dihydrocapsaicin).
Figure 6:
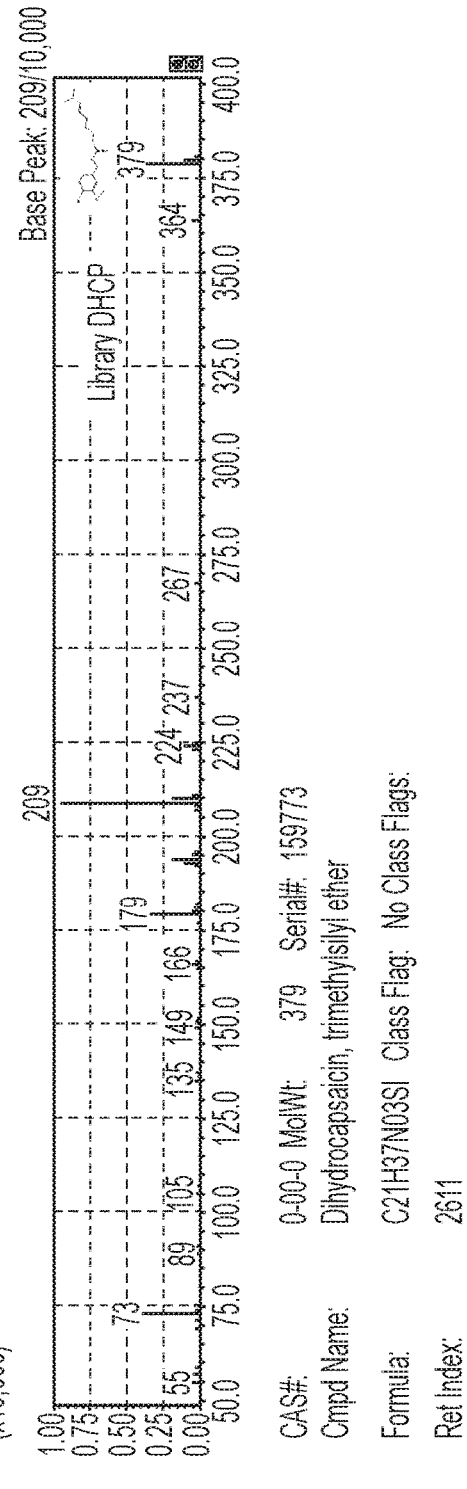
Figure 6:
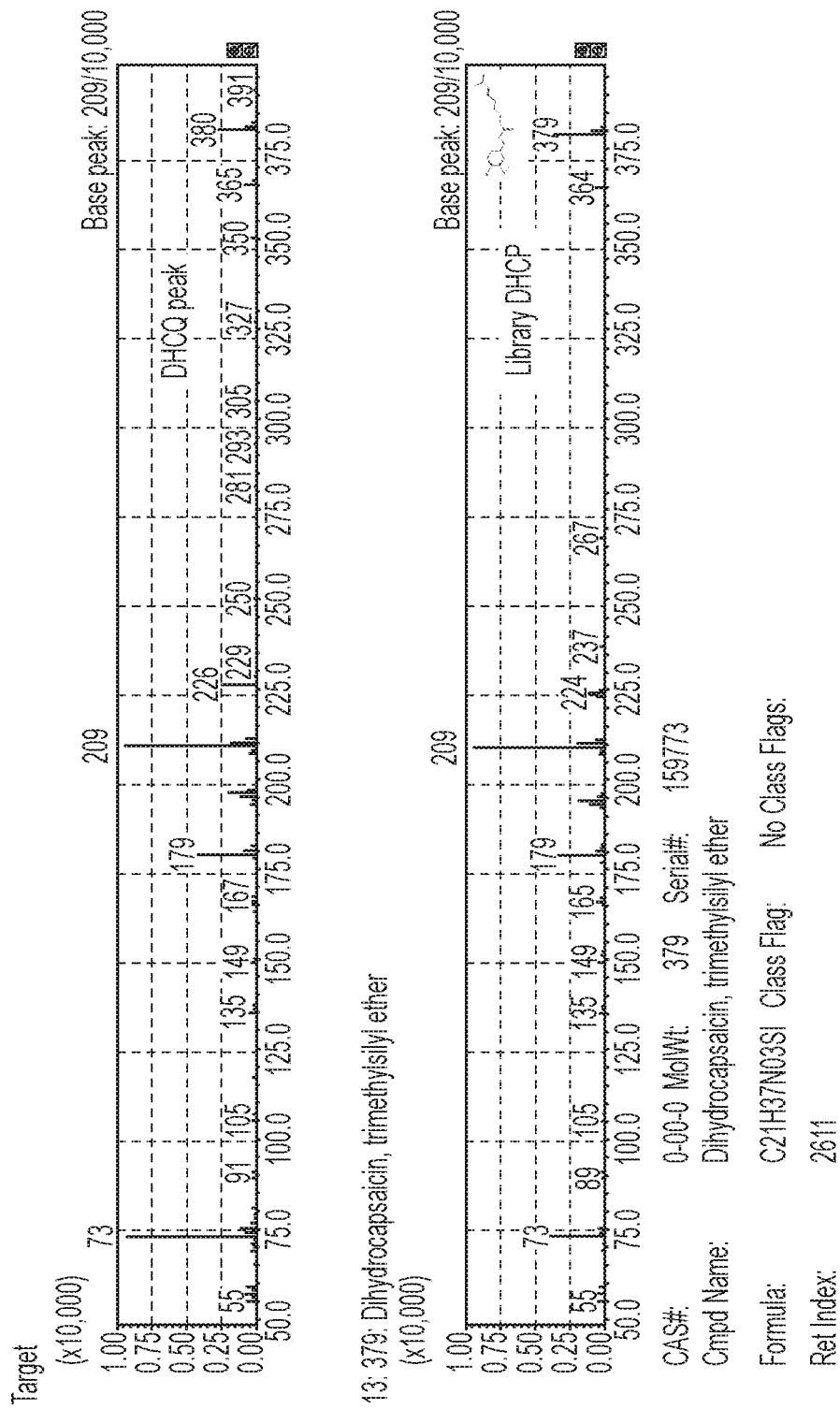

Next, GC/MS analysis was performed to confirm the identity of CQ and DHCQ in the induced cultures. The GC/MS analysis was performed with a Shimadzu GC-2010 system coupled with a GC/MS-QP2010S detector. Column Rtx-5MS (thickness 0.25 u; length 30 m; diameter 0.25 mm) was used for separation. The injection temperature was 265° C., the injection mode was split, and the oven temperature was 140° C. The temperature gradient was as follows: 0-1 min, 140° C.; 1-11.25 min, 140° C. to 263° C., rate 12; 11.25-21.25 min, 263° C. The GC/MS spectra obtained for CQ and DHCQ from the induced cultures are shown in FIG. 5. These spectra were then compared to the standard spectrum for DHCP (dihydrocapsaicin) from the MS library in the GC/MS machine. DHCP was the closest match to CQ and DHCQ because the MS library did not contain a standard for CQ or DHCQ. Since DHCQ is one Dalton heavier than DHCP and CQ is one Dalton less than DHCP, the identity of CQ and DHCQ in the samples was firmly established by the GC/MS profiles (FIG. 6). These results show that the ACS1 and CS/AT3/Pun1 genes can be used to produce capsinoids by biosynthesis using VA and either 6E or 8M as starting materials.

REFERENCES

Hachiya S, Kawabata F, Ohnuki K, Inoue N, Yoneda H, Yazawa S and Fushiki T (2007). "Effects of CH-19 Sweet, a Non-Pungent Cultivar of Red Pepper, on Sympathetic Nervous Activity, Body Temperature, Heart Rate, and Blood Pressure in Humans," Biosci. Biotechnol. Biochem, 71: 671-676, Han K, Jeong H J, Sung J, Keum Y S, Cho M C, Kim J H, Kwon J K, Kim B D, Kang B C (2013) Biosynthesis of capsinoid is controlled by the Pun1 locus in pepper. Molecular Breeding, 31: 537-548.

Handler S, Rorvik D (2008): PDR for Nutritional Supplements Second Edition. Thomas Reuters.

He G.-J. et al. (2009), European Journal of Medicinal Chemistry 44: 3345-3349.

Inoue N. et al. (2007), Biosci Biotechnol Biochem 71: 380-389.

Iwai K, Yazawa A, Watanabe T. (2003) Roles as metabolic regulators of the non-nutrients, capsaicin and capsiate, supplemented to diets. Proc Jpn Acad.; 79:207-212.

Kawabata F. et al. (2006), Biosci Biotechnol Biochem 70:2824-2835.

Kobata K, Todo T, Yazawa S, Iwai K, Watanabe T (1998) Novel capsaicinoid-like substances, capsiate and dihydrocapsiate, from the fruits of a nonpungent cultivar, CH-19 Sweet, of pepper (Capsicum annuum L.). Journal of Agricultural and Food Chemistry, 46: 1695-1697.

Kobata K, Sutoh K, Todo T, Yazawa S, Iwai K, Watanabe T (1999) Nordihydrocapsiate, a new capsinoid from the fruits of a nonpungent pepper, Capsicum annuum. Journal of Natural Products, 62: 335-336.

Macho A, Lucena C, Sancho R, Daddario N, Minassi A, Munoz E, Appendino G. (2003) "Non-pungent Capsaicinoids from Sweet Pepper Synthesis and Evaluation of the Chemopreventive and Anticancer Potential." Eur. J. Nutr., 42: 2-9.

Masuda Y, Haramizu S, Oki K, Ohnuki K, Watanabe T, Yazawa S, Kawada T, Hashizume S, Fushiki T (2003) Upregulation of uncoupling proteins by oral administration of capsiate, a nonpungent capsaicin analog. Journal of Applied Physiology, 95: 2408-2415.

Ohnuki K, Niwa S, Maeda S, Inoue N, Yazawa S, Fushiki T. (2001) CH-19 sweet, a non-pungent cultivar of red pepper, increased body temperature and oxygen consumption in humans. Biosci Biotechnol Biochem., 65:2033-2036.

Sancho R, Lucena C, Macho A, Caizado M, Bianco-Molina M, Minassi A, Appendino G and Munoz E. (2002) "immunosuppressive Activity of Capsaicinoids: Capsiate Derived from Sweet Peppers inhibits NF-kappaB Activation and is a Potent Anti-inflammatory Compound in Vivo." Eur. J. Immunol. 32: 1753-1763.

Snitker S, Fujishima Y, Shen H, Ott S, Pi-Sunyer X, Furuhata Y, Sato H, Takahashi M (2009) Effects of novel capsinoid treatment on fatness and energy metabolism in humans: possible pharmacogenetic implications. American Journal of Clinical Nutrition, 89: 45-50.

Szallasi A, Blumberg P M, Annicelli L L, Krause J E, Cortright D N (1999) The cloned rat vanilloid receptor VR1 mediates both R-type binding and C-type calcium response in dorsal root ganglion neurons. Mol Pharmacol 56:581-587.

Yazawa S, Suetome N, Okamoto K, Namiki T (1989) Content of capsaicinoids and capsaicinoid-like substances in fruit of pepper (Capsicum annuum L.) hybrids made with "CH-19 Sweet" as a Parent. Journal of the Japanese Society for Horticultural Science, 58: 601-607.

What is claimed is:

1. A method of producing a capsinoid, the method comprising:
   (a) expressing a recombinant capsiate synthase (CS) in a cellular system;
   (b) adding 8-methyl-6-nonenoyl-CoA and vanillyl alcohol to the cellular system; and
   (c) incubating the cellular system to produce the capsinoid.

2. A method of producing a capsinoid, the method comprising:
   (a) expressing a capsiate synthase (CS) and an acyl-CoA synthetase (ACS) in a cellular system;
   (b) adding a medium chain fatty acid and vanillyl alcohol to the cellular system; and
   (c) incubating the cellular system to produce the capsinoid;
      wherein: the CS comprises an amino acid sequence having at least 90% identity to SEQ ID NO: 1, the ACS comprises an amino acid sequence having at least 90% identity to SEQ ID NO: 2; and the cellular system comprises yeasts, bacteria, and/or combinations thereof.

3. The method of claim 1, wherein the CS amino acid sequence is derived from a plant of the *Capsicum* genus.

4. The method of claim 3, wherein the *Capsicum* genus plant is a ghost chili plant.

5. The method of claim 1, wherein the CS comprises an amino acid sequence having at least 90% identity to SEQ ID NO: 1.

6. The method of claim 5, wherein the CS comprises the amino acid sequence of SEQ ID NO: 1.

7. The method of claim 6, wherein the method further comprises expressing a recombinant acyl-CoA synthetase (ACS) in the cellular system, and wherein the ACS amino acid sequence is derived from a plant of the *Capsicum* genus.

8. The method of claim 7, wherein the *Capsicum* genus plant is a ghost chili plant.

9. The method of claim 8, wherein the ACS comprises an amino acid sequence having at least 90% identity to SEQ ID NO: 2.

10. The method of claim 9, wherein the ACS comprises the amino acid sequence of SEQ ID NO: 2.

11. The method of claim 10, wherein the cellular system is selected from the group including yeast, non-capsinoid producing plants, algae and bacteria.

12. The method of claim 11, wherein the cellular system is bacteria.

13. The method of claim 12, wherein the cellular system is *E. Coli*.

14. The method of claim 13, wherein the method further comprises collecting the produced capsinoid, capsiate or dihydrocapsiate.

15. The method of claim 14, wherein the method further comprises purifying the produced capsinoid, capsiate or dihydrocapsiate to a purity of greater than 70% by weight.

16. The method of claim 2, wherein the CS comprises the amino acid sequence of SEQ ID NO: 1.

17. The method of claim 16, wherein the ACS comprises the amino acid sequence of SEQ ID NO: 2.

18. The method of claim 2, wherein the cellular system is bacteria.

19. The method of claim 18, wherein the cellular system is *E. Coli*.

20. The method of claim 2, wherein the method further comprises collecting the produced capsinoid, capsiate or dihydrocapsiate.

21. The method of claim 20, wherein the method further comprises purifying the produced capsinoid, capsiate or dihydrocapsiate to a purity of greater than 70% by weight.

* * * * *

SEQUENCE LISTING

<160> NUMBER OF SEQ ID NOS: 4

<210> SEQ ID NO 1
<211> LENGTH: 440
<212> TYPE: PRT
<213> ORGANISM: Capsicum annuum L

<400> SEQUENCE: 1

```
Met Ala Phe Ala Leu Pro Ser Ser Leu Val Ser Val Cys Asp Lys Ser
1               5                   10                  15

Phe Ile Lys Pro Ser Ser Leu Thr Pro Ser Lys Leu Arg Phe His Lys
            20                  25                  30

Leu Ser Phe Ile Asp Gln Ser Leu Ser Asn Met Tyr Ile Pro Cys Ala
        35                  40                  45

Phe Phe Tyr Pro Lys Val Gln Gln Arg Leu Glu Asp Ser Lys Asn Ser
    50                  55                  60

Asp Glu Leu Ser His Ile Ala His Leu Leu Gln Thr Ser Leu Ser Gln
65                  70                  75                  80

Thr Leu Val Ser Tyr Tyr Pro Tyr Ala Gly Lys Leu Lys Asp Asn Ala
                85                  90                  95

Thr Val Asp Cys Asn Asp Met Gly Ala Glu Phe Leu Ser Val Arg Ile
            100                 105                 110

Lys Cys Ser Met Ser Glu Ile Leu Asp His Pro His Ala Ser Leu Ala
        115                 120                 125

Glu Ser Ile Val Leu Pro Lys Asp Leu Pro Trp Ala Asn Asn Cys Glu
    130                 135                 140

Gly Gly Asn Leu Leu Val Val Gln Val Ser Lys Phe Asp Cys Gly Gly
145                 150                 155                 160

Ile Ala Ile Ser Val Cys Phe Ser His Lys Ile Gly Asp Gly Cys Ser
                165                 170                 175

Leu Leu Asn Phe Leu Asn Asp Trp Ser Ser Val Thr Arg Asp His Thr
            180                 185                 190

Thr Thr Ala Leu Val Pro Ser Pro Arg Phe Val Gly Asp Ser Val Phe
        195                 200                 205

Ser Thr Lys Lys Tyr Gly Ser Leu Ile Thr Pro Gln Ile Leu Ser Asp
    210                 215                 220

Leu Asn Glu Cys Val Gln Lys Arg Leu Ile Phe Pro Thr Asp Lys Leu
225                 230                 235                 240

Asp Ala Leu Arg Ala Lys Val Ala Glu Glu Ser Gly Val Lys Asn Pro
                245                 250                 255

Thr Arg Ala Glu Val Val Ser Ala Leu Leu Phe Lys Cys Ala Thr Lys
            260                 265                 270

Ala Ser Ser Ser Met Leu Pro Ser Lys Leu Val His Phe Leu Asn Ile
        275                 280                 285

Arg Thr Met Ile Lys Pro Arg Leu Pro Arg Asn Ala Ile Gly Asn Leu
    290                 295                 300

Ser Ser Ile Phe Ser Ile Glu Ala Thr Asn Met Gln Asp Met Glu Leu
305                 310                 315                 320

Pro Thr Leu Val Arg Asn Leu Arg Lys Glu Val Glu Val Ala Tyr Lys
                325                 330                 335

Lys Asp Gln Val Glu Gln Asn Glu Leu Ile Leu Glu Val Val Glu Ser
            340                 345                 350

Met Arg Glu Gly Lys Leu Pro Phe Glu Asn Met Asp Gly Tyr Glu Asn
        355                 360                 365
```

-continued

```
Val Tyr Thr Cys Ser Asn Leu Cys Lys Tyr Pro Tyr Thr Val Asp
    370                 375                 380

Phe Gly Trp Gly Arg Pro Glu Arg Val Cys Leu Gly Asn Gly Pro Ser
385                 390                 395                 400

Lys Asn Ala Phe Phe Leu Lys Asp Tyr Lys Ala Gly Gln Gly Val Glu
                405                 410                 415

Ala Arg Val Met Leu His Lys Gln Gln Met Ser Glu Phe Glu Arg Asn
            420                 425                 430

Glu Glu Leu Leu Glu Phe Ile Ala
        435                 440
```

<210> SEQ ID NO 2
<211> LENGTH: 658
<212> TYPE: PRT
<213> ORGANISM: Capsicum annuum L.

<400> SEQUENCE: 2

```
Met Ala Thr Asp Lys Phe Ile Ile Glu Val Glu Ser Ala Lys Pro Ala
1               5                   10                  15

Lys Asp Gly Arg Pro Ser Met Gly Pro Val Tyr Arg Ser Ile Phe Ala
            20                  25                  30

Lys His Gly Phe Pro Pro Ile Pro Gly Leu Asp Ser Cys Trp Asp
        35                  40                  45

Ile Phe Arg Met Ser Val Glu Lys Tyr Pro Asn Asn Arg Met Leu Gly
    50                  55                  60

Arg Arg Glu Ile Val Asp Gly Lys Pro Gly Lys Tyr Val Trp Met Ser
65                  70                  75                  80

Tyr Lys Glu Val Tyr Asp Ile Val Lys Val Gly Asn Ser Ile Arg
                85                  90                  95

Ser Ile Gly Val Asp Val Gly Asp Lys Cys Gly Ile Tyr Gly Ala Asn
            100                 105                 110

Cys Pro Glu Trp Ile Ile Ser Met Glu Ala Cys Asn Ala His Gly Leu
        115                 120                 125

Tyr Cys Val Pro Leu Tyr Asp Thr Leu Gly Ala Gly Ala Val Glu Phe
    130                 135                 140

Ile Ile Ser His Ala Glu Val Thr Ile Ala Phe Val Glu Glu Lys Lys
145                 150                 155                 160

Leu Pro Glu Leu Leu Lys Thr Phe Pro Asn Ala Ser Lys Tyr Leu Lys
                165                 170                 175

Thr Ile Val Ser Phe Gly Lys Val Thr Pro Glu Gln Lys Lys Glu Leu
            180                 185                 190

Glu Glu Phe Gly Val Val Leu Tyr Ser Trp Asp Glu Phe Leu Gln Leu
        195                 200                 205

Gly Ser Gly Lys Gln Phe Asp Leu Pro Val Lys Lys Glu Asp Ile
    210                 215                 220

Cys Thr Ile Met Tyr Thr Ser Gly Thr Gly Asp Pro Lys Gly Val
225                 230                 235                 240

Leu Ile Ser Asn Thr Ser Ile Val Thr Leu Ile Ala Gly Val Arg Arg
                245                 250                 255

Phe Leu Gly Ser Val Asp Glu Ser Leu Asn Val Asp Asp Val Tyr Leu
            260                 265                 270

Ser Tyr Leu Pro Leu Ala His Ile Phe Asp Arg Val Ile Glu Glu Cys
        275                 280                 285

Phe Ile His His Gly Ala Ser Ile Gly Phe Trp Arg Gly Asp Val Lys
    290                 295                 300
```

```
Leu Leu Thr Glu Asp Ile Gly Glu Leu Lys Pro Thr Val Phe Cys Ala
305                 310                 315                 320

Val Pro Arg Val Leu Asp Arg Ile Tyr Ser Gly Leu Gln Gln Lys Ile
            325                 330                 335

Ala Ala Gly Gly Phe Leu Lys Ser Thr Leu Phe Asn Leu Ala Tyr Ala
        340                 345                 350

Tyr Lys His His Asn Leu Lys Lys Gly Arg Lys His Phe Glu Ala Ser
            355                 360                 365

Pro Leu Ser Asp Lys Val Val Phe Ser Lys Val Lys Glu Gly Leu Gly
        370                 375                 380

Gly Arg Val Arg Leu Ile Leu Ser Gly Ala Ala Pro Leu Ala Ala His
385                 390                 395                 400

Val Glu Ala Phe Leu Arg Val Val Ala Cys Cys His Val Leu Gln Gly
            405                 410                 415

Tyr Gly Leu Thr Glu Thr Cys Ala Gly Thr Phe Val Ser Leu Pro Asn
        420                 425                 430

Arg Tyr Asp Met Leu Gly Thr Val Gly Pro Pro Val Pro Asn Val Asp
            435                 440                 445

Val Cys Leu Glu Ser Val Pro Glu Met Ser Tyr Asp Ala Leu Ser Ser
450                 455                 460

Thr Pro Arg Gly Glu Val Cys Val Arg Gly Asp Val Leu Phe Ser Gly
465                 470                 475                 480

Tyr Tyr Lys Arg Glu Asp Leu Thr Lys Glu Val Met Ile Asp Gly Trp
            485                 490                 495

Phe His Thr Gly Asp Val Gly Glu Trp Gln Pro Asn Gly Ser Leu Lys
        500                 505                 510

Ile Ile Asp Arg Lys Lys Asn Ile Phe Lys Leu Ser Gln Gly Glu Tyr
            515                 520                 525

Val Ala Val Glu Asn Leu Glu Asn Ile Tyr Gly Asn Asn Pro Ile Ile
530                 535                 540

Asp Ser Ile Trp Ile Tyr Gly Asn Ser Phe Glu Ser Phe Leu Val Ala
545                 550                 555                 560

Val Ile Asn Pro Asn Gln Arg Ala Val Glu Gln Trp Ala Glu Val Asn
            565                 570                 575

Gly Leu Ser Gly Asp Phe Ala Ser Leu Cys Glu Lys Pro Glu Val Lys
        580                 585                 590

Glu Tyr Ile Leu Arg Glu Leu Thr Lys Thr Gly Lys Glu Lys Lys Leu
            595                 600                 605

Lys Gly Phe Glu Phe Leu Lys Ala Val His Leu Asp Pro Val Pro Phe
610                 615                 620

Asp Met Glu Arg Asp Leu Leu Thr Pro Thr Phe Lys Lys Lys Arg Pro
625                 630                 635                 640

Gln Leu Leu Lys Tyr Tyr Lys Asp Val Ile Asp Ser Met Tyr Lys Gly
            645                 650                 655

Thr Lys
```

<210> SEQ ID NO 3
<211> LENGTH: 1323
<212> TYPE: DNA
<213> ORGANISM: Capsicum annuum L.

<400> SEQUENCE: 3 atggctttg cattaccatc atcacttgtt tcagtttgtg acaaatcttt tatcaaacct      60

```
tcctctctca ccccctctaa acttagattt cacaagctat ctttcatcga tcaatcttta     120
agtaatatgt atatcccttg tgcattttt  taccctaaag tacaacaaag actagaagac     180
tccaaaaatt ctgatgagct ttcccatata gcccacttgc tacaaacatc tctatcacaa     240
actctagtct cttactatcc ttatgcagga aagttgaagg acaatgctac tgttgactgt     300
aacgatatgg gagctgagtt cttgagtgtt cgaataaaat gttccatgtc tgaaattctt     360
gatcatcctc atgcatctct tgcagagagc atagttttgc ccaaggattt gccttgggcg     420
aataattgtg aaggtggtaa tttgcttgta gttcaagtaa gtaagtttga ttgtggggga     480
atagccatca gtgtatgctt ttcgcacaag attggtgatg gttgctctct gcttaatttc     540
cttaatgatt ggtctagcgt tactcgtgat catacgacaa cagctttagt tccatctcct     600
agatttgtag gagattctgt cttctctaca aaaaaatatg gttctcttat tacgccacaa     660
attttgtccg atctcaacga gtgcgtacag aaaagactca ttttcctac  agataagtta     720 gatgcacttc gagctaaggt ggcagaagaa tcaggagtaa aaaatccaac aagggcagaa     780
gttgttagcg ctcttctttt caaatgtgca acaaaggcat catcatcaat gctaccatca     840
aagttggttc acttcttaaa catacgtact atgatcaaac ctcgtctacc acgaaatgcc     900
attggaaatc tctcgtctat tttctccata gaagcaacta acatgcagga catggagttg     960
ccaacgttgg ttcgtaattt aaggaaggaa gttgaggtgg catacaagaa agaccaagtc    1020
gaacaaaatg aactgatcct agaagtagta gaatcaatga gagaagggaa actgccatt t   1080 gaaaatatgg atggctatga gaatgtgtat acttgcagca atctttgcaa atatccgtac    1140
tacactgtag attttggatg gggaagacct gaaagagtgt gtctaggaaa tggtccctcc    1200
aagaatgcct tcttcttgaa agattacaaa gctgggcaag gcgtggaggc gcgggtgatg    1260
ttgcacaagc aacaaatgtc tgaatttgaa cgcaatgagg aactccttga gttcattgcc    1320
taa                                                                  1323
```

<210> SEQ ID NO 4
<211> LENGTH: 1977
<212> TYPE: DNA
<213> ORGANISM: Capsicum annuum L.

<400> SEQUENCE: 4

```
atggctacgg acaaatttat tattgaagtt gaatcagcaa aaccggcaaa agatggtcgc      60
ccgagcatgg gcccggtcta tcgttcgatc tttgcgaaac atggctttcc gccgccgatc     120
ccgggtctgg attcatgctg gacattttt  cgtatgtcgg tggaaaaata tccgaacaat     180
cgcatgctgg gccgtcgcga aattgttgat ggcaaaccgg gtaaatacgt ttggatgagc     240
tacaaagaag tctacgacat cgttatcaaa gtcggtaaca gtattcgttc catcggcgtg     300
gatgttggtg acaaatgcgg catttatggt gcaaactgtc cggaatggat tatcagcatg     360
gaagcatgca atgctcatgg cctgtattgt gtcccgctgt acgataccct gggcgcaggt     420
gctgtggaat ttattatctc tcacgcgaa  gtgaccatcg ccttcgttga agagaaaaaa     480
ctgccggaac tgctgaaaac ctttccgaat gcgagcaaat atctgaaaac cattgtctct     540
ttcggcaaag tgacgccgga acagaagaaa gaactggaag aatttggtgt ggttctgtac     600
agttgggatg aatttctgca gctgggctcc ggtaaacaat tcgatctgcc ggtgaaaaag     660
aaagaagata tttgcaccat catgtatacg agcggcacca cgggtgatcc gaaaggtgtg    720
ctgatttcaa acacctcgat tgtgacgctg atcgccggtc ttcgtcgctt tctgggctca     780
gttgatgaat cgctgaatgt ggatgacgtt tatctgtcat acctgccgct ggcacatatt     840
```

```
tttgaccgtg tgatcgaaga atgcttcatt catcacggcg cttcgatcgg tttttggcgc    900
ggcgatgtga aactgctgac cgaagacatt ggcgaactga aaccgacggt tttctgtgcg    960
gtcccgcgtg tgctggatcg catctattca ggtctgcagc aaaaaattgc ggccggcggt   1020
tttctgaaat cgaccctgtt caacctggcg tatgcctaca aacatcacaa tctgaagaaa   1080
ggccgcaaac actttgaagc cagcccgctg tctgataaag tcgtgttcag taaagtgaaa   1140
gaaggcctgg gcggtcgtgt tcgcctgatt ctgtccggtg cggctccgct ggccgcacat   1200
gtggaagcgt ttctgcgtgt tgtcgcctgc tgtcacgttc tgcagggcta tggtctgacc   1260
gaaacgtgcg caggcacctt cgtgagtctg ccgaaccgct acgatatgct gggcacggtt   1320
ggtccgccgg tcccgaatgt cgatgtgtgc ctggaaagcg tgccggaaat gtcttatgac   1380
gctctgagct ctaccccgcg tggtgaagtt tgtgtccgcg gcgatgttct gttttccggt   1440
tattacaaac gtgaagacct gaccaaagaa gttatgattg atggctggtt ccatacgggc   1500
gacgtcggtg aatggcagcc gaacggtagc ctgaaaatca tcgatcgtaa gaaaaacatc   1560
ttcaaactgt ctcaaggcga atatgtggcc gttgaaaacc tggaaaatat ttacggcaac   1620
aatccgatta tcgacagcat ttggatctat ggtaacagtt ttgaatcctt cctggtcgcg   1680
gtgatcaacc cgaatcagcg tgcagtcgaa caatgggctg aagtgaatgg cctgagtggt   1740
gatttcgcct ccctgtgtga aaaaccggaa gtgaaagaat acattctgcg cgaactgacc   1800
aaaacgggca aagagaaaaa actgaaaggt ttcgaatttc tgaaagcagt tcatctggac   1860
ccggtgccgt ttgatatgga acgtgacctg ctgaccccga cgttcaagaa aaaacgtccg   1920
caactgctga aatactataa agatgtgatc gactcaatgt ataaaggcac gaaataa     1977
```